United States Patent [19]

Majoie

[11] 4,287,209

[45] Sep. 1, 1981

[54] DERIVATIVES OF PHENOXYALKYLCARBOXYLIC ACIDS

[75] Inventor: Bernard Majoie, Dijon, France

[73] Assignee: Societe de Recherches Industrielles (S.O.R.I.), France

[21] Appl. No.: 1,011

[22] Filed: Jan. 4, 1979

Related U.S. Application Data

[62] Division of Ser. No. 714,504, Aug. 16, 1976, Pat. No. 4,146,385.

[30] Foreign Application Priority Data

Aug. 20, 1975 [GB] United Kingdom .............. 34689/75

[51] Int. Cl.$^3$ .................... A61K 31/215; C07C 69/66
[52] U.S. Cl. ...................................... 424/308; 560/52
[58] Field of Search ................... 560/9, 20, 21, 45, 52, 560/57, 455 R, 599; 562/426, 436, 435, 452, 468, 460, 464, 471; 71/100, 108, 109, 116, 117, 121, 122, 123; 424/301, 308, 309, 317, 319, 331, 333

[56] References Cited

U.S. PATENT DOCUMENTS

| | | | |
|---|---|---|---|
| 3,326,933 | 6/1967 | Wright | 562/471 |
| 3,362,997 | 1/1968 | Bolhofer | 260/600 |
| 3,363,003 | 1/1968 | Bolhofer | 260/613 |
| 3,833,648 | 9/1974 | Moriyama et al. | 562/460 |
| 3,907,792 | 9/1975 | Mieville | 560/52 |
| 4,072,705 | 2/1978 | Mieville | 560/52 |
| 4,088,474 | 5/1978 | Matterstock | 560/57 |
| 4,146,385 | 3/1979 | Majoie | 71/116 |

OTHER PUBLICATIONS

Mieville, Chem. Absts., 85, 192382(a), 1976.
Clarke et al., Chem. Absts., 60, 11295(h), 1964.
Duc, Orzneim.-Forsch., (Drug Res.) 26, 5, 894–895, 1976.
Sornay et al., Arzneim-Forsch., (Drug Res.) 26, 5, 885–889 (1976).

*Primary Examiner*—G. T. Breitenstein
*Attorney, Agent, or Firm*—Bacon & Thomas

[57] ABSTRACT

The invention provides novel phenoxyalkylcarboxylic acids which are useful in therapy as metabolic regulators and in agriculture as selective herbicides.

11 Claims, No Drawings

DERIVATIVES OF PHENOXYALKYLCARBOXYLIC ACIDS

This is a division of application Ser. No. 714,504, filed Aug. 16, 1976, now U.S. Pat. No. 4,146,385.

The present invention concerns, by way of new industrial products, derivatives of phenoxyalkylcarboxylic acids of the formula ($I_o$) given later. It also relates to the processes for the synthesis of the products of the formula ($I_o$) as well as to their application in therapy and in agriculture.

It is known that p-carbonylphenoxyalkylcarboxylic acids, their ester derivatives and amide derivatives have already been proposed as hypocholesterolaemic and hypolipidaemic agents, in particular in British Pat. Nos. 1,268,321 and 1,415,295. It has now been found, surprisingly, that the corresponding m-carbonylphenoxyalkylcarboxylic acids, esters and amides, on the one hand, and the derivatives of the said compounds which result from the conversion of the carbonyl group CO into the —CH(OH)—, —CH(O-alkyl)—, —CH(OCOCH$_3$)—, —CH$_2$— and —C(=CH$_2$)— group, on the other, are valuable products in therapy and agriculture.

The compounds according to the invention are characterised in that they correspond to the general formula ($I_o$) given later in the appendix, in which R represents a hydrogen atom, a $C_1$-$C_{19}$-alkyl group having a linear or branched hydrocarbon chain, or a group of the formulae Ia, Ib, Ic and Id given in the appendix (where $X_1$ and $X_2$, which may be identical or different, each represent a H, F, Cl, Br, I, OH, or a $C_1$-$C_4$-alkyl, $C_1$-$C_4$-alkoxy, $CF_3$, $SCH_3$, $SCF_3$, $OCF_3$, CHO, $CO_2H$, $CO_2CH_3$, $CO_2C_2H_5$ and $OCOCH_3$ group, $X_3$ represents O and S and $X_4$ represents H, Cl and Br).

R' and R", which may be identical or different, each represent a hydrogen atom or a $C_1$-$C_4$-alkyl group, X represents a hydrogen atom, a $C_1$-$C_4$-alkyl, $C_1$-$C_4$-alkoxy, hydroxyl, $NO_2$ or $NH_2$ group or a halogen atom chosen from amongst F, Cl and Br, Y represents H, OH, a $C_1$-$C_{12}$-alkoxy group (of which the hydrocarbon radical has a linear or branched chain), a $C_3$-$C_8$-cycloalkoxy group, a $C_1$-$C_4$-alkylthio group, a 2,3-dihydroxypropoxy group, a 3-pyridyl-methyleneoxy group, a 5-(2-methyl-3-hydroxy-4-hydroxymethylpyridiyl)-methyleneoxy group of the formula Ie given in the appendix, and an $NZ_1Z_2$, $NH(CH_2)_mNZ_1Z_2$, $O(CH_2)_mNZ_1Z_2$ and $O(CH_2)_mCONZ_1Z_2$ group (where m=2, 3 or 4, $Z_1$ and $Z_2$ are $C_1$-$C_4$-alkyl groups and $Z_1$ and $Z_2$ considered together can form, with the nitrogen atom to which they are bonded, an N-heterocyclic group of 5 to 7 ring members which can contain a second hetero-atom such as O and N and can be substituted) and Z represents a —CO—, —C(=CH$_2$)—, —C(CH$_3$)OH— and —CHR'''— group (where R''' represents a hydrogen atom or a hydroxyl, acetoxy and $C_1$-$C_4$-alkoxy group), and their salts, especially those obtained with inorganic or organic bases if Y is OH, and those obtained with inorganic and organic acids if Y contains a basic radical.

The process of preparation, according to the invention, of a derivative of a phenoxyalkylcarboxylic acid of the formula $I_o$ (where R, R', R", X, Y and Z are defined as above), which comprises the synthesis of a carbonyl compound (Z=CO) by two parallel routes followed, where appropriate, by the conversion of the said carbonyl group into C(CH$_3$)OH and C(=CH$_2$) groups, on the one hand, and to a CHR''' group, on the other, is characterised in that a carbonyl compound of the formula I given in the appendix (where R, R', R", X and Y are defined as above) is prepared by one of the following two routes (a) and (b):

(a) An m-hydroxyketone of the formula IV, given in the appendix (where R and X are defined as above) is reacted with a reactant choser from amongst the group consisting of a bromo-derivative of the formula BrC(R'R")COY (where R', R" and Y are defined as above), on the one hand, and a mixture of acetone and chloroform, on the other, the product of the formula I (where R'=R"=CH$_3$ and Y=OH) obtained according to the reaction with the acetone/chloroform mixture being converted, where appropriate, to a compound of the formula I where Y is different from OH, in accordance with a method which is in itself known, or (b) an m-bromoether compound of the formula VI given in the appendix (where R', R" and X are defined as above and T' and T" each represent a $C_1$-$C_4$ lower alkyl group (preferably CH$_3$), and T' and T" considered together can form a —CH$_2$CH$_2$— group) is reacted with an alkyl-lithium of the formula TLi (where T is an alkyl group, preferably butyl) to form an organo-lithium compound of the formula V given in the appendix (where X, R', R", T' and T" are defined as above), and thereafter the said organo-lithium compound of the formula V is reacted with a sodium carboxylate of the formula $RCO_2Na$ (where R is defined as above) to form a compound of the formula VII given in the appendix (where R, R', R", X, T' and T" are defined as above), the said compound of the formula VII being converted, in the presence of $H^+$ ions, into an aldehyde of the formula I (Y=H), the oxidation of the said aldehyde giving an acid of the formula I (Y=OH) which in its turn is capable of being converted to an ester and amide of the formula I (Y≠OH), in that, if necessary, the compound of the formula I thus obtained is subjected to a reduction reaction with CH$_3$MgI to give a carbinol of the formula IIa given in the appendix (where R, R', R", X and Y are defined as above), it being possible in turn to subject the said carbinol of the formula IIa to a dehydration reaction to form an ethylenic compound of the formula II given in the appendix (where R, R', R", X and Y are defined as above), in that, if necessary, the said compound of the formula I is subjected to a reduction with an alkali metal hydride, especially potassium borohydride, and sodium borohydride, to form a carbinol compound of the formula III given in the appendix (where R''' is OH and R, R', R", X and Y are defined as above), the said carbinol of the formula III (R'''=OH) thereafter being subjected, if necessary, to an esterification reaction to give a compound of the formula III, where R''' is OCOCH$_3$, on the one hand, and to an etherification reaction, to give a compound of the formula III where R''' is a $C_1$-$C_4$-alkoxy group, on the other, and in that, if necessary, the said compound of the formula I is subjected to a WOLFF-KISCHNER reduction reaction, namely a reduction of a carbonyl group to a methyl group, to give a compound of the formula III where R''' is H.

Though it is possible, according to this process, to envisage directly obtaining compounds of the formula $I_o$, where COY forms an ester or amide radical, it is frequently more practical first to form a compound of the formula I, where Y is OH or $C_1$-$C_4$-alkoxy (especially $OCH_3$ and $OC_2H_5$) and thereafter to form (a) the other esters and amides of the formula I by esterification or trans-esterification or amidification respectively (starting from the corresponding acid chloride or by trans-amidification starting especially from the methyl or ethyl ester), or (b) the acids or esters of the formulae IIa, II or III from the said acids or lower alkyl esters of the formula I, followed, where appropriate, by conversion of the lower alkyl esters of the formulae IIa, II and III to the corresponding acids, or, where appropriate, by conversion of the acids and lower alkyl esters to other esters and amides according to item (a) above, whilst taking into account possible incompatibility of the methods of reduction of the Z=CO group with the various values of Y.

Amongst the $C_1$-$C_{19}$-alkyl groups which fall under the definition of R, there may especially be mentioned the methyl, ethyl, isopropyl, propyl, butyl, isobutyl, tertiary butyl, 2-pentyl, 3-pentyl, n-pentyl, n-octyl, n-dodecyl, n-hexadecyl, n-heptadecyl, n-octadecyl, 2-octadecyl and n-nonadecyl groups.

The alkyl, alkoxy and alkylthio groups according to the invention possess a hydrocarbon radical with a linear or branched chain; amongst the $C_1$-$C_4$ hydrocarbon radicals of the said alkyl, alkoxy and alkylthio groups, the preferred radical for $X_1$, $X_2$, R', R", X and R''' is the methyl radical.

The preferred radicals $Z_1$ and $Z_2$ are, on the other hand, H, $CH_3$, $C_2H_5$, $CH(CH_3)_2$ and n-$C_4H_9$.

For Y, the $C_1$-$C_{12}$-alkoxy groups include the following preferred radicals: methoxy, ethoxy, isopropoxy, isobutoxy, tertiary butoxy, 2-pentyloxy, 3-pentyloxy, 1-cetyloxy and dodecyloxy.

By N-heterocyclic $NZ_1Z_2$ groups with 5 to 7 ring members, which are optionally substituted, there are especially understood the pyrrolidino, morpholino, piperidino, 4-methylpiperazino, 4-(p-chlorophenyl)-piperazino and hexamethyleneimino groups; amongst the groups Y containing at least one nitrogen atom, the preferred groups $Y=NZ_1Z_2$ are the $N(CH_3)_2$, $N(C_2H_5)_2$, $N(n-C_4H_9)_2$, piperidino and morpholino groups; the preferred groups for $Y=NH-(CH_2)_m-NZ_1Z_2$ are the 2-dimethylaminoethylamino and 2-diethylaminoethylamino groups; the preferred groups for $Y=O(CH_2)_m-NZ_1Z_2$ are the hexamethyleneiminoethoxy, morpholinoethoxy, piperidinoethoxy and 2-diethylaminoethoxy groups.

Amongst the salts of the compounds of the formula $I_o$, particularly suitable examples are the pharmaceutically acceptable salts obtained with organic and inorganic bases if Y=OH and the addition salts with inorganic and organic acids, in particular with hydrochloric, oxalic, fumaric and maleic acids, if Y contains a basic organic group.

The compounds of the formula $I_o$ can be used in therapy, especially as metabolic regulators. In fact, they act simultaneously on the cholesterol, the lipids and the uric acid.

Their mechanism of action as hypocholesterolaemic agents results in the fact that they also act on cholersis.

Furthermore, alongside this property, which they all share, of acting as metabolic regulators, certain products have anti-inflammatory and/or diuretic effects.

Furthermore, the compounds of the formula $I_o$ are useful substances in agriculture as selective herbicides acting in particular against casual plants.

Depending on the value of Z, the invention relates to the compounds of the formulae I, IIa, II and III given in the appendix (where R, R', R", R''', Y and X are defined as above).

The compounds IIa and II, on the one hand, and III, on the other, are in fact directly derived from the compounds of the formula I, as indicated earlier. The conversion of I to IIa and to II is illustrated by diagram A given in the appendix, according to which I is reacted with the organo-magnesium compound $CH_3MgI$ to give the carbinol IIa which in turn, by dehydration, gives the ethylenic compound II.

The conversion of I to II is illustrated by the diagram B given in the appendix, according to which a compound I (where Y is especially $OCH_3$ or $OC_2H_5$) is reduced either (a) by the WOLFF-KISCHNER method to give a compound of the formula III, where R'''=H, or (b) with $KBH_4$ to give the carbinol III, where R'''=OH, which in turn ($b_1$) by hydrolysis in the presence of $OH^-$ gives the acid VIII, ($b_2$) by acetylation with acetyl chloride gives the carbinol acetate III, where R'''=OAc, the hydrolysis of the said acetate in the presence of $OH^-$ giving the acid VIII, or ($b_3$) by etherification (treatment with NaH followed by $CH_3I$) gives the carbinol ether III where R'''=$OCH_3$, the said ether giving the acid IX by hydrolysis in the presence of $OH^-$.

The compounds of structure 1 can in turn be prepared in accordance with two methods:

Via an m-hydroxyketone of the formula IV given in the appendix (where R and X are defined as above), which is itself obtained according to three methods (A, B or C, illustrated below), or via a compound having a potential carboxyl group, of the formula VI given in the appendix (where X, R", R''', T' and T" are defined as above), by attaching it to the rest of the molecule by method C.

I. METHOD VIA A HYDROXYKETONE

Method A:

This can be used each time the radical R can be fixed in the desired position by a FRIEDEL-CRAFTS reaction (FC); the method is carried out in accordance with the reaction mechanism illustrated in diagram C. A compound RH (where R is defined as above) is reacted by the Friedel-Crafts method with an m-nitrobenzoyl chloride of the formula X to give an m-nitroketone of the formula XI, the $NO_2$ group of the said m-nitroketone is reduced selectively to give an m-aminoketone of the formula XI and the latter, by diazotisation, gives the m-hydroxyketone IV.

The following should be noted with regard to the use of this method:

If a substituent (X, or one of the substituents of R) is incompatible with the Friedel-Crafts reaction (OH or $NH_2$), the latter can be employed provided this substituent is blocked, or, preferably, if the substituent is generated after the Friedel-Crafts reaction; where the substituent is blocked (with a methyl or acetyl radical), unblocking will be carried out at the last stage;

the selective reduction of $NO_2$ to $NH_2$ is carried out either chemically ($SnCl_2$/HCl) or catalytically (Raney Ni or Pd on charcoal), the latter method always being preferred unless one of the substituents of A is Br or Cl; and it is possible to envisage carrying out the Friedel-Crafts reaction with a meta-methoxybenzoyl chloride of the formula XIII given in the appendix in order to obtain the m-hydroxyketone IV more directly; equally it is possible to envisage carrying out the Friedel-Crafts reaction with the compound of the formula XIV given in the appendix.

Method B:

this can be summarised according to the reaction scheme of diagram D given in the appendix; a bromoderivative R—Br is reacted with Li or an alkyl-lithium such as BuLi to give R—Li, which is reacted with a sodium m-methoxybenzoate of the formula XV given in the appendix to form an m-methoxyketone of the formula XVI, which is demethylated to give IV.

Method C:

the same principle is followed as in method B, reversing the roles played by Br and by the $Co_2Na$ group, as indicated in diagram E given in the appendix, according to which the bromo-derivative of the formula XVII is treated with BuLi to give the organo-lithium compound XVIII, which is treated with the carboxylate $RCO_2Na$ to give XVI, which is demethylated as in the preceding method.

Methods B and C are thus equivalent and require the following comments:

If $X=NO_2$ or $NH_2$, the two methods B and C should be avoided;

if one of the substituents of R or of X represents OH, a reactant wherein this OH group is blocked is used as the starting material;

other organo-metallic compounds (magnesium compounds or cadmium compounds) can replace the organo-lithium compounds, but the latter are preferred because they generally yield purer "methoxyketones", and it is also noted that the said organo-lithium compounds can be reacted with a tertiary amide according to the equation $RLi+XIX=XVI$; and the demethylation of the ethers is always carried out with the aid of aluminium chloride except if one of the substituents of R is $CF_3$; in that case, 48% strength hydrobromic acid, or pyridinium hydrochloride are used.

The three methods (A, B and C) are thus capable of yielding all the m-hydroxyketones IV employed; the latter are new in the majority of cases and thus form part of the invention, as intermediate products. The products of the formula IV have been listed in Table I below, specifying the methods (A, B or C) which can be used to obtain them and underlining the preferred method or methods.

The m-hydroxyketones of the formula IV are thereafter converted to compounds of the formula I in accordance with methods which are in themselves known, which have been shown schematically in diagram F below.

In general, the acetone/chloroform method is employed systematically if it is desired to obtain compounds I where $R'=R''=CH_3$, provided that an excessively alkaline mediium is not detrimental to the substituents of R; in all other cases, the condensation of $BrC(R',R'')COY$ is carried out with IV, and this method is particularly preferred if R carries a $CF_3$ group (which is labile to sodium hydroxide) or even a fluorine atom; on this assumption, it is the high purity of the final product thus obtained which is valuable.

II. METHOD VIA A COMPOUND HAVING A POTENTIAL CARBOXYL GROUP

This is the second route mentioned above for the synthesis of the compounds of the formula I, which involves a compound having a potential carboxyl group. The reaction mechanism has been given in diagram G below (where, for convenience, T' and T'' considered together form a $-CH_2CH_2-$ group), which shows that in its first part the present technique employs method C. In fact, an m-bromophenol of the formula XX is reacted with a chloro-1,3-dioxolane of the formula XXI to give the derivative VI (which is a homologue of the m-bromoether of the formula XVII), which is reacted with BuLi to give V which in its turn is reacted with $RCO_2Na$ to give VII, the acid hydrolysis of VII giving the corresponding aldehyde I (Y=H), which is oxidised so as to give the corresponding acid I (Y=OH).

As the presence of the Li atom on the compound V is incompatible with the carbonyl and carboxyl groups, the latter are formed in the last stages.

All the remarks made with regard to carrying out method C apply to this process II; furthermore, the oxidation of the aldehyde to the acid (carried out with $KMnO_4$ or $AgNO_3$) excludes the possibility of obtaining compounds I where R=H.

Preparation examples which in no way imply a limitation have been given below to illustrate the various methods of synthesis which have been mentioned above.

PREPARATION I

Production of [m-(2-phenoxy-2-methyl-propionic)acid][p-chlorophenyl]-carbinol (compare formula XXII). Alternative nomenclature:

2-methyl-2-[3-(α-hydroxy-4-chlorobenzyl)phenoxy]-propionic acid (1) Production of 4'-chloro-3-nitrobenzophenone 30.5 g (0.27 mol) of chlorobenzene an 36 g (0.27 mol) of aluminium chloride are introduced into a 250 cm³ flask and 25 g (0.135 mol) of m-nitrobenzoyl chloride dissolved in 15 cm³ of chlorobenzene are added dropwise. The mixture is heated for 5 hours at between 50° and 60° C. and is then allowed to cool and is hydrolysed with 500 g of ice+20 cm³ of concentrated HCl (d=1.18); the batch is extracted with ether and the extract is washed with aqueous sodium hydroxide solution (strength 30 g/l) and then with water; the ether phase is dried, decolorised and then evaporated in vacuo; 26 g of the expected ketone are obtained. Melting point 97° C.

(2) Production of 4'-chloro-3-aminobenzophenone 77.1 g (0.342 mol) of $SnCl_2$ and 105 cm³ of concentrated HCl (d=1.18) are placed in a 500 cm³ flask; the mixture is heated gently to produce complete dissolution, and 30 g (0.114 mol) of the preceding nitroketone are added all at once; the mixture is slowly heated to 80° C. and from there onwards the very exothermic reaction takes place; the heating is replaced by a bath of cold water required to keep the mixture at the boil; as soon as the temperature drops, the heating is resumed so as to maintain the reaction mixture at 100° C. for 2 hours; after cooling, the mixture is poured into 1 liter of water and is rendered basic with sodium hydroxide solution. The amine precipitates and is extracted with ether, and after drying and evaporation of the solvent 21 g of the expected amine are recovered. Melting point 118° C.

(3) Production of 4'-chloro-3-hydroxybenzophenone 25 cm³ of concentrated HCl (d=1.18)+250 cm³ of water are introduced into a 500 cm³ Erlenmeyer flask, with magnetic stirring; 25 g of the preceding product are added so as to prepare its hydrochloride and the mixture is cooled to about 5° C., this temperature being maintained constant to ±2° C. 7.5 g of sodium nitrite dissolved in 30 cm³ of water are added; the mixture is left in this way for 2 hours, throughout at +5° C.; at the end, 50 mg of urea are added and the diazonium salt is pourea, in small portions of about 20 to 30 cm³, into a mixture of 700 cm³ of toluene, 250 cm³ of water and 20 cm³ of concentrated sulphuric acid (d=1.83); the whole is stirred well and heated to 100° C. This decomposes the diazonium salt. The organic phase is separated off and left in the cold; the pure phenol crystallises from the toluene and is filtered off, giving 20.5 g of the expected product. Melting point 154° C.

(4) Production of 2-methyl-2-[3-(p-chlorobenzoyl)-phenoxy]propionic acid (compare formula XXIII)

200 cm³ of anhydrous acetone, 23 g (0.576 mol) of sodium hydroxide and 22.5 g (0.096 mol) of the preceding phenol are introduced into a 500 cm³ flask; the whole is heated under reflux for 30 minutes and a mixture of 34.5 g (0.288 mol) of chloroform and of 70 cm³ of acetone is added dropwise. The mixture is heated under reflux for 5 hours, the acetone is then evaporated in vacuo and water is added; the basic aqueous phase is washed with ether and then acidified; it is then extracted several times with ether and the combined ether phases are extracted with a saturated sodium bicarbonate solution; this new basic phase is acidified and the expected acid precipitates. Weight: 21 g; melting point 144° C. When recrystallised from 125 cm³ of a water-ethanol mixture (30:70, volume/volume), the melting point is raised to 146° C.

(5) Production of isopropyl 2-methyl-2-[4-(p-chlorobenzoyl)phenoxy]-propionate (compare formula XXIV)

100 cm³ of benzene, 5 cm³ of isopropyl alcohol, 0.9 g of p-toluenesulphonic acid and 8.5 g of the preceding acid are introduced into a 250 cm³ flask surmounted by a Dean and Stark device and a condenser. The mixture is heated under reflux for 12 hours. After cooling, ether is added and the mixture is washed with aqueous sodium hydroxide solution (strength 30 g/l) and then with water; the organic phase is dried, decolorised and evaporated in vacuo. An oil remains, which crystallises gradually. The ester is recrystallised from 75 cm³ of hexane and 6.8 g of expected product are obtained. Melting point 57° C.

(6) Production of the corresponding carbinol ester (compare formula XXV) Nomenclature: Isopropyl 2-methyl-2-[3-(α-hydroxy-4-chlorobenzyl)-phenoxy]-propionate 3.6 g of the preceding ester (obtained in paragraph 5) are dissolved in 30 cm³ of methanol at 40° C. in an Erlenmeyer flask; 700 mg of potassium borohydride are added and the mixture is left for 2 hours at the same temperature, with magnetic stirring; the solvent is then evaporated and the residue is taken up with ether and water; the ether phase is washed with 10% strength HCl and then with sodium bicarbonate (strength 20 g/l). It is then dried and concentrated in vacuo; 3.6 g of the expected alcohol-ester are obtained; the compound is oily and gives only a single spot in thin layer chromatography (in benzene/ethyl acetate (10:1): Rf=0.4); refractive index $n_D$ (at 20° C.)=1.543.

(7) Production of the expected carbinol acid of the formula XXII

Saponification of the preceding ester in 4 N aqueous sodium hydroxide solution gives this acid, which is recrystallised in quantitative yield from benzene. Melting point 116° C.

PREPARATION II

Production of 2-methyl-2-[3-(p-trifluoromethylbenzoyl)phenoxy]-propionic acid (compare formula XXVI)

(1) Preparation of 4'-trifluoromethyl-3-methoxybenzophenone

This is carried out under nitrogen at −60° C. 0.29 mol (65 g) of para-bromo-trifluoromethylbenzene dissolved in 100 ml of anhydrous ether is added dropwise to 0.29 mol of butyl-lithium in solution in ether (1.48 mol/liter). The reaction is followed by gas phase chromatography; when there is no longer any remaining para-bromo-trifluoromethylbenzene, 0.29 mol (50.5 g) of sodium 3-methoxybenzoate is added. The mixture is allowed to return to ambient temperature. After stirring for 64 hours, it is hydrolysed in iced water. The batch is extracted with ether. The ether phase is dried, decolorised and concentrated. 45 g of a product which has been recrystallised from a mixture of isopropyl ether and hexane are obtained. Melting point 69° C. Yield: 55%.

(2) Preparation of 4'-trifluoromethyl-3-hydroxy-benzophenone 0.11 mol (31 g) of the preceding product and 0.55 mol (63.5 g) of pyridinium hydrochloride are heated under reflux for 1 hour 30 minutes. The mixture is taken up in 10% strength hydrochloric acid and then extracted with ether, and the extract is washed with water. After extraction with N sodium hydroxide solution, this extract is acidified and extracted with ether; the ether phase is dried, decolorised and concentrated. The product is obtained in the form of a white solid. Melting point 130° C. Weight: 21 g. Yield: 72%.

(3) Preparation of ethyl 2-methyl-2-[3-(p-trifluoromethylbenzyl)-phenoxy]-propionate (compare formula XXVII)

$7.8 \times 10^{-2}$ mols (3.1 g) of sodium hydroxide is added to $7.8 \times 10^{-2}$ mols (21 g) of the preceding product dissolved in 150 cm³ of ethanol. When the sodium hydroxide has dissolved, $10 \times 10^{-2}$ mols (19.5 g) of ethyl bromoisobutyrate is added and the mixture is heated under reflux for 24 hours. The reaction mixture is then concentrated and the residue is taken up in ether. The ether mixture is washed with aqueous sodium hydroxide solution (strength 5 g/l) and then with water until neutral. The organic phase is dried, decolorised and concentrated; 14.5 g of solid product are obtained. Yield: 49%. Melting point 50° C.

(4) Preparation of the expected acid, of the formula XXVI

About 10 ml of aqueous sodium hydroxide of strength 40 g/l are added to 9 g ($2.4 \times 10^{-2}$ mol) of the preceding ester, dissolved in 70 ml of methanol. The reaction mixture is stirred for 4 hours at ambient temperature and is then concentrated, and the residue is taken up in water, acidified and extracted with ether. The organic phase is washed with water and extracted with an aqueous Na bicarbonate solution (strength 20 g/l). The aqueous phase is washed with ether and acidified. It is extracted with ether and the extract is then washed with water until its pH is neutral. The ether phase is dried, decolorised and concentrated. 4.5 g of a white solid, which is recrystallised from isopropyl ether, are obtained. Yield: 54%. Melting point 133° C.

PREPARATION III

Production of 2-methyl-2-[3-(m-chlorobenzoyl)-phenoxy]propionic acid (compare formula XXVIII)

(1) Preparation of 3'-chloro-3-methoxybenzophenone 0.2 mol of butyl-lithium (a suspension in ether, containing 1.8 mol/liter) is placed in a 500 cm$^3$ flask; it is cooled to $-20°$ C. and 37.4 g (0.2 mol) of meta-bromoanisole diluted with 50 cm$^3$ of anhydrous ether are added dropwise; when the addition has ended, the mixture is stirred for 10 to 15 minutes at the same temperature and 15.7 g (0.1 mol) of meta-chlorobenzoic acid dissolved in the minimum amount of THF are added dropwise; the temperature is allowed to return to ambient temperature and the reaction mixture is stirred for 2 hours under these conditions; it is then poured onto water, the ether is decanted and the aqueous phase is extracted with ether; the combined ether phases are washed with sodium bicarbonate and then with water, dried, decolorised and concentrated in vacuo. 26 g of a solid melting at 52° C. are obtained.

Note: it is possible to employ the Li or Na salt of this acid directly in the reaction; in that case, it is necessary to introduce it dry and in a stoichiometric amount relative to the m-bromoanisole.

(2) Preparation of 3'-chloro-3-hydroxybenzophenone 26 g of the ether obtained above in (1) and 60 cm$^3$ of chlorobenzene are introduced into a 250 cm$^3$ single-necked flask and 35 g of aluminium chloride are added a little at a time; the reaction mixture is then heated under reflux for 30 minutes, allowed to cool to about 60° C. and then poured onto a mixture of ice and concentrated hydrochloric acid (d=1.18); this mixture is stirred for 1 hour and the solid is then filtered; the latter is washed with petroleum ether to free it from the last traces of chlorobenzene; the phenol thus obtained (20 g) melts at 104° C. and can be used without further purification.

(3) Preparation of the expected acid of the formula XXVIII 33 g of the preceding phenol, 400 cm$^3$ of anhydrous acetone and 32 g of sodium hydroxide are introduced into a 1,000 cm$^3$ 3-necked flask; the mixture is heated under reflux for 15 minutes; the heating is then stopped and a mixture of chloroform in 80 cm$^3$ is added dropwise; the addition is exothermic and maintains the reflux until ⅔ of the mixture has been added; for the remaining one-third it is necessary to apply external heat to maintain the reflux; the mixture is left at the boil for 2 hours after the end of the addition and the acetone is then driven off in vacuo. The residue is taken up in water; this alkaline aqueous phase is washed twice with ether, then acidified and again extracted with ether; the ether phase, which contains the expected acid and the phenol which has not reacted, is washed with sodium bicarbonate (strength 20 g/l); this new aqueous phase, when acidified at 0° C. with good stirring, precipitates the expected acid; when recrystallised from hexane, the acid melts at 98° C. Weight: 27 g.

PREPARATION IV

Production of 3-(α-furoyl)-phenoxyacetic acid (compare formula XXIX)

(1) Preparation of the dimethylacetal of 3-bromo-phenoxyacetaldehyde

A mixture of 350 cm$^3$ of anhydrous C$_2$H$_5$OH, 17.3 g (0.1 mol) of 3-bromophenol, 5.6 g (0.1 mol) of potassium hydroxide and 15 g (0.12 mol) of chloroacetaldehyde dimethylacetal is heated under reflux for 5 hours; at the end of the reaction, the mixture is filtered, the alcohol is evaporated and the residue is taken up in ether; the ether phase is washed with aqueous sodium hydroxide solution (of strength 20 g/l) and then with water until neutral; this ether phase is dried, decolorised with animal charcoal and then concentrated in vacuo; the oily residue is distilled in vacuo; the expected product passes over at 98°–100° C. under 0.1 mm Hg. Weight: 24 g; yield: 92%.

(2) Preparation of 3-(α-furoyl)-phenoxyacetaldehyde (compare formula XXX)

13.1 g (0.1 mol) of the preceding derivative are dissolved in 50 cm$^3$ of anhydrous ether; this solution is cooled to $-15°$ C. and 0.105 mol of a solution of butyl-lithium in ether (1.6 mol/liter) is added dropwise thereto; when the addition has ended, 13.65 g (0.105 mol) of anhydrous sodium 2-furoate are added in small amounts of about 5 g, whilst constantly maintaining a temperature of $-15°$ C.; this addition is carried out in the course of 10 minutes, the temperature is then allowed to return to ambient temperature and the mixture is stirred under these conditions for 17 hours. Thereafter, the reaction mixture is hydrolysed with 500 cm$^3$ of water; the batch is extracted with ether and the ether phase is washed with N sodium hydroxide solution and then with water, dried, decolorised and concentrated in vacuo. The oil which remains (15 g) is taken up in 50 cm$^3$ of alcohol+5 cm$^3$ of concentrated hydrochloric acid (d=1.18); this mixture is boiled for 5 hours under reflux, the alcohol is driven off and the residue is taken up in ether; this ether phase is washed with N sodium hydroxide solution, dried and concentrated; the residue is distilled in vacuo; 11.5 g of the expected aldehyde, passing over at 143°–144° C. under 0.05 mm Hg are obtained; yield: 50%.

(3) Preparation of the expected acid, of the formula XXIX 10 g of the preceding aldehyde (2) are suspended in 50 cm$^3$ of water; whilst constantly stirring vigorously, a suspension of silver oxide prepared from 8.5 g of silver nitrate and 30 cm$^3$ of 4 N sodium hydroxide solution is added; stirring is then continued for 3 hours at ambient temperature after which the mixture is filtered on a Büchner funnel; the solution containing sodium hydroxide is acidified to pH 1 at 0° C. with 6 N hydrochloric acid; the expected acid precipitates. After recrystallisation from ethanol, 7 g of the acid are obtained. Melting point 126° C.

A certain number of compounds according to the invention have been listed in Tables II, III and IV below.

Furthermore, the pharmacological results recorded on some products in the test described below have been summarised in Table V:

At $T_o$ and T+15 hours, the animals (WISTAR ♂ rats, of 250–300 g) are orally given a dose of 100 mg/kg (esters) or 50 mg/kg (acids) of product in suspension in a 3% strength solution of gum in water.

The hypolipidaemic and hypocholesterolaemic activity is determined by calculating the percentage reduction in the total lipids content and total cholesterol content between $T_o$ and T+39 hours; this percentage is corrected in accordance with the reduction in the contents of the same parameters in a comparison batch which is given two intubations of water containing gum.

The rats are caused to fast from $T_o-15$ hours and remain fasting throughout the duration of the experiment.

Amongst the products of great value from the point of view of hypolipidaemia and hypocholesteroleamia, there may especially be mentioned 2-methyl-2-[3-(4-chlorobenzoyl)phenoxy]-propionic acid, 2-methyl-2-[3-(3-chlorobenzoyl)phenoxy]-propionic acid, 2-methyl-2-[3-(3-trifluoromethylbenzoyl)-phenoxy]-propionic acid, 2-methyl-2-[3-(4-methyl-3-fluorobenzoyl)-phenoxy]-propionic acid, 2-methyl-2-[3-(4-trifluoromethylbenzoyl)-phenoxy]-propionic acid, 2-methyl-2-[3-(α-hydroxy-4-bromobenzyl)-phenoxy]-propionic acid, 2-methyl-2-[3-(α-hydroxy-4-bromobenzyl)-phenoxy]-propionic acid and 2-methyl-2-[3-(4-chlorobenzyl)-phenoxy]-propionic acid, their metal salts and their esters, especially the methyl, ethyl and isopropyl esters.

According to the invention, therapeutic compositions are proposed which are useful especially in the treatment of illnesses of the cardiovascular system, characterised in that they contain at least one compound of the formula $I_o$, or one of its pharmaceutically acceptable salts, in association with a physiologically acceptable excipient.

The compounds of the formula $I_o$ can be administered to man, especially, by oral administration, injection or implantation. The preferred method of administration for the esters and amides is oral administration, whilst the acids are preferably administered by injection in the form of metal salts (especially salts of sodium, potassium, magnesium, zinc and aluminium).

The selective herbicidal properties of the compounds of the formula $I_o$ have been assessed especially with regard to casual graminaceae. For this purpose, seeds of cultivated plants (wheat and barley) and of casual graminaceae (foxtail and wild oats) were sown in pots and grown in a greenhouse. They are watered with aqueous solutions or suspensions of compounds of the formula $I_o$ when the plants have three to four leaves, and with a known comparison product, 2-(2,4-dichlorophenoxy)-propionic ... (sic), each substance being administered at a rate of application of the order of 0.80 to 1.20 kg/ha. It is found that the products according to the invention, after several weeks (for example 4 weeks) of treatment, do not destroy the cereals but do destroy the two casual graminaceae.

In agriculture, the compounds according to the invention can be administered in the usual forms, especially as a wettable powder, as an emulsion and/or as granules.

APPENDIX

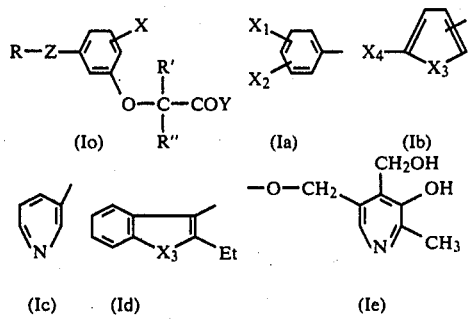

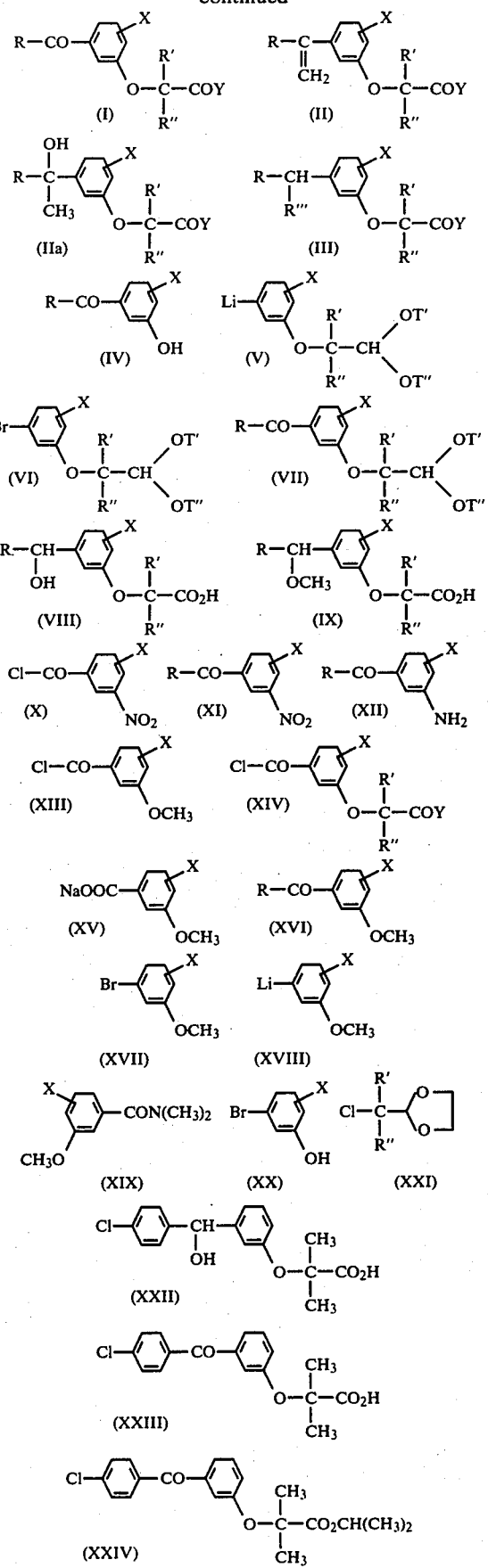

-continued
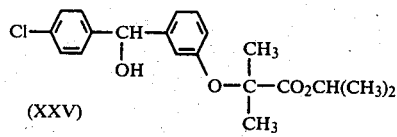
(XXV)
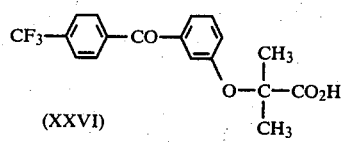
(XXVI)
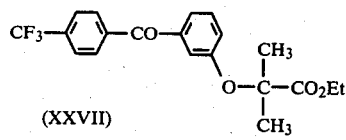
(XXVII)
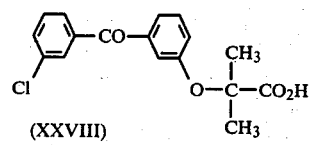
(XXVIII)
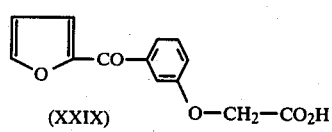
(XXIX)
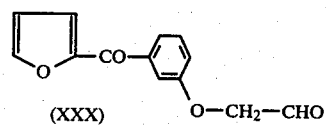
(XXX)
DIAGRAM A
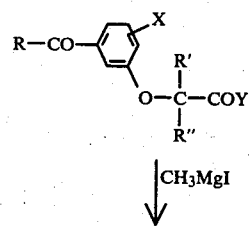
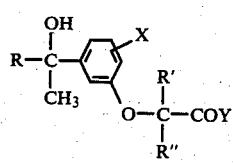
(IIa)
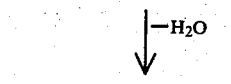
(II)
DIAGRAM B
-continued
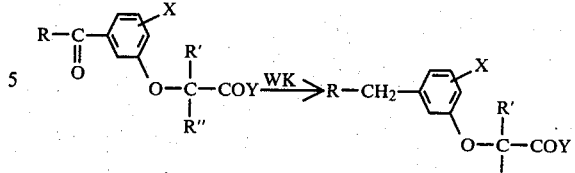
(I)    (III; R''' = H)
WK: WOLFF-KISCHNER reduction
↓ KBH₄
(VIII)      (III; R''' = OH)
↓ CH₃COCl    ↓ NaH, ICH₃
(III; R''' = OAc)    (III; R''' = OCH₃)
↓ OH⁻
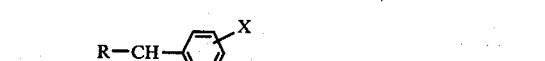
(IX)
DIAGRAM C
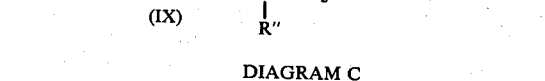
(X)     (XI)
(XII)     (IV)
DIAGRAM D
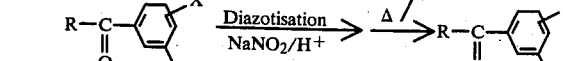
DIAGRAM E
(XVII)    (XVIII)

DIAGRAM F
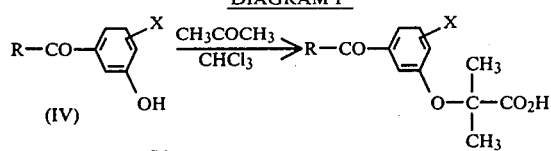
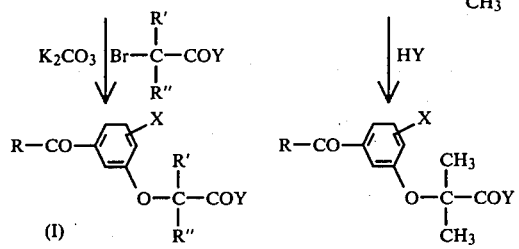
DIAGRAM G
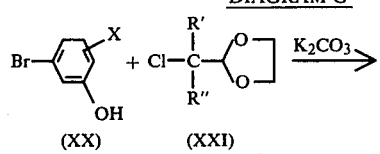
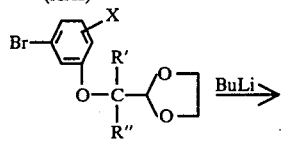
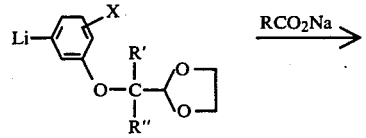
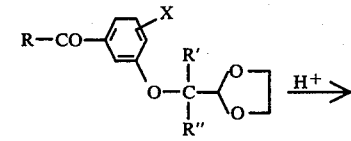
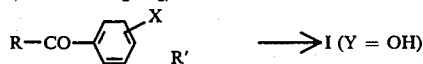
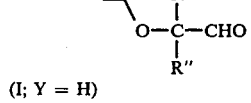
TABLE I
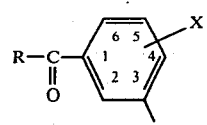
| R | X | M.P., °C. | METHODS |
|---|---|---|---|
| Cl—φ— | —6 Cl | 172 | A, B |
| Br—φ— | H | 170 | A, B, C |
| φ—(Cl) | H | 104 | B, C |
| F—φ— | H | 105 | A, B, C |
| φ—(CF₃) | H | 78 | B, C |
| CH₃—φ— | H | 121 | A, B, C |
| φ—(Br) | H | 110 | B, C |
| n-C₄H₉ | H | 67 | B |
| CH₃—φ—(F) | H | 120 | A, |
| φ—(Cl) | H | 126 | B, C |
| Cl—φ—(Cl) | H | 140 | C |
| φ—(F) | H | 64 | B, C |
| Cl—φ—(Cl) | H | 70 | A, C |
| Me—φ—(Me) | H | 116 | A |
TABLE II
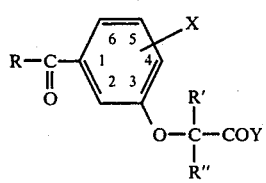
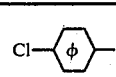
| Compound No. | Code No. | R | R' | R'' | X | Y | M.P., °C. | $n_D^{20}$ | Method of production |
|---|---|---|---|---|---|---|---|---|---|
| 1 | 451 | Cl—φ— | CH₃ | CH₃ | H | OH | 149 | | I A |

TABLE II-continued structure:
R—C(=O)—[phenyl with positions 1,2,3,4,5,6; X at 4]—O—C(R')(R'')—COY

| Compound No. | Code No. | R | R' | R'' | X | Y | M.P., °C. | $n_D^{20}$ | Method of production |
|---|---|---|---|---|---|---|---|---|---|
| 2 | 467 A | Cl—φ— | CH₃ | CH₃ | H | O—CH(CH₃)₂ | 57 | | |
| 3 | 467 B | Cl—φ— | CH₃ | CH₃ | H | O Et | 50 | | |
| 4 | 467 C | Cl—φ— | CH₃ | CH₃ | H | O CH₃ | 75 | | |
| 5 | 514 | Cl—φ— | CH₃ | H | H | O—CH(CH₃)₂ | 59 | | |
| 6 | 539 | Cl—φ— | CH₃ | H | H | OH | 140 | | I A |
| 7 | 561 | Br—φ— | CH₃ | CH₃ | H | OH | 145 | | I B |
| 8 | 561 A | Br—φ— | CH₃ | CH₃ | H | O—CH(CH₃)₂ | 82 | | |
| 9 | 576 | φ— (Cl meta) | CH₃ | CH₃ | H | OH | 98 | | I C |
| 10 | 576 A | φ— (Cl meta) | CH₃ | CH₃ | H | O—CH(CH₃)₂ | — | 1.548 | |
| 11 | 597 | Cl—φ— | CH₃ | CH₃ | H | O(—CH₂)₂—N(hexamethyleneimine) oxalate | 138 | | |
| 12 | 599 | φ— | CH₃ | CH₃ | H | OH | 90 | | I A |
| 13 | 599 A | φ— | CH₃ | CH₃ | H | OCH₃ | 60 | | |
| 14 | 600 | H₃CO—φ— | CH₃ | CH₃ | H | OH | 98 | | I* |
| 15 | 600 A | H₃CO—φ— | CH₃ | CH₃ | H | O—CH(CH₃)₂ | — | 1.5485 | |
| 16 | 601 | CH₃— | CH₃ | CH₃ | H | OH | 102 | | I** |
| 17 | 601 A | CH₃— | CH₃ | CH₃ | H | O—CH(CH₃)₂ | — | 1.500 | |
| 18 | 623 | F—φ— | CH₃ | CH₃ | H | OH | 119 | | I B |
| 19 | 629 | F—φ— | CH₃ | CH₃ | H | O—CH(CH₃)₂ | — | 1.530 | |

TABLE II-continued

R—C(=O)—[benzene ring with positions 1-6, X at position 5]—O—C(R')(R'')—COY

| Compound No. | Code No. | R | R' | R'' | X | Y | M.P., °C. | $n_D^{20}$ | Method of production |
|---|---|---|---|---|---|---|---|---|---|
| 20 | 650 | (CF₃-φ-) | CH₃ | CH₃ | H | OH | 80 | | I B |
| 21 | 663 | (F-φ-) | CH₃ | CH₃ | H | OCH₃ | 48 | | |
| 22 | 671 | (H₃C-φ-) | CH₃ | CH₃ | H | OH | 98 | | I A |
| 23 | 682 | (Br-φ-) | CH₃ | CH₃ | H | OH | 95 | | I B |
| 24 | 685 | nC₄H₉ | CH₃ | CH₃ | H | OH | 58 | | I B |
| 25 | 686 | (H₃C-φ(F)-) | CH₃ | CH₃ | H | OH | 110 | | I A |
| 26 | 690 | (φ(Cl)-) | CH₃ | CH₃ | H | OH | 88 | | I C |
| 27 | 691 | (F₃C-φ-) | CH₃ | CH₃ | H | OH | 138 | | I B |
| 28 | 699 | (Cl-φ(Cl)-) | CH₃ | CH₃ | H | OH | 114 | | I C |
| 29 | 704 | (Br-φ-) | CH₃ | CH₃ | H | OCH₃ | 50 | | |
| 30 | 710 | (Cl-φ(Cl)-) | CH₃ | CH₃ | H | OH | 114 | | I C |
| 31 | 712 | (Me-φ(Me)-) | CH₃ | CH₃ | H | OH | 98 | | I A |
| 32 | | (Me-φ(Me)-) | CH₃ | CH₃ | H | OCH₃ | 70 | | |
| 33 | | (Cl-φ-) | H | H | H | OH | 132 | | II |
| 34 | | (F-φ-) | H | H | H | OH | 103 | | II |
| 35 | | (Cl-φ-) | CH₃ | CH₃ | H | N(Et)(Et) | 96 | | |
| 36 | | (Cl-φ-) | CH₃ | CH₃ | H | morpholino | 126 | | |

TABLE II-continued

Structure:
R—C(=O)—[phenyl ring positions 1,2,3,4,5,6, with X at position 4/5]—O—C(R')(R'')—COY

| Compound No. | Code No. | R | R' | R'' | X | Y | M.P., °C. | $n_D^{20}$ | Method of production |
|---|---|---|---|---|---|---|---|---|---|
| 37 | 467 D | Cl—φ— | CH₃ | CH₃ | H | —O(—CH₂)₃—C(=O)—N(Me)Me | 73 | | |
| 38 | | F—φ— | CH₃ | CH₃ | H | —O C₈H₁₇ | | 1.529 | |
| 39 | | F—φ— | CH₃ | CH₃ | H | —O C₁₄H₂₉ | | 1.5306 | |
| 40 | | F—φ— | CH₃ | CH₃ | H | —S—Et | | 1.5289 | |
| 41 | | CF₃—φ— | CH₃ | CH₃ | H | piperidinyl (N) | 131 | | |
| 42 | | CF₃—φ— | CH₃ | CH₃ | H | O(—CH₂)₂—C(=O)—N(Me)Me | 58 | | |
| 43 | | CF₃—φ— | CH₃ | CH₃ | H | O—CH₂—(2,3,6-trisubstituted phenyl: CH₂OH, OH, CH₃) | 102 | | |
| 44 | 561 B | Br—φ— | CH₃ | CH₃ | H | —O—C₁₄H₂₉ | 49 | | |
| 45 | 561 C | Br—φ— | CH₃ | CH₃ | H | —O—CH₂—(pyridyl), HCl | 141 | | |
| 46 | 561 D | Br—φ— | CH₃ | CH₃ | H | —O—(CH₂)₂—N(Et)Et, HCl | 81 | | |
| 47 | | thienyl | CH₃ | CH₃ | H | OH | 108 | | II |
| 48 | | thienyl | H | H | H | OH | 120 | | II |
| 49 | | Cl-thienyl | CH₃ | CH₃ | H | OH | 124 | | II |
| 50 | | furyl | CH₃ | CH₃ | H | OH | 100 | | II |
| 51 | | furyl | H | H | H | OH | 126 | | II |
| 52 | | benzofuryl-Et | CH₃ | CH₃ | H | OH | 105 | | II |
| 53 | | Cl—φ— | CH₃ | CH₃ | 6 Cl | OH | 139 | | I B |
| 54 | | Cl—φ— | CH₃ | CH₃ | 4 OH | OH | 188 | | I*** |

TABLE II-continued $$R-\underset{\underset{O}{\|}}{C}-\underset{\underset{2\ 3}{\overset{6\ 5}{\bigcirc}}}{\phantom{C}}\overset{X}{\underset{\underset{R''}{\overset{R'}{|}}}{\phantom{C}}}$$
$$O-\underset{\underset{R''}{|}}{\overset{R'}{C}}-COY$$

| Compound No. | Code No. | R | R' | R" | X | Y | M.P., °C. | $n_D^{20}$ | Method of production |
|---|---|---|---|---|---|---|---|---|---|
| 55 |  | 3-pyridyl | CH₃ | CH₃ | H | OH | 144 |  | II |
| 56 | 722 | φ— | CH₃ | CH₃ | H | NH—(CH₂)₂—N(Et)(Et) fumarate | 110 |  |  |
| 57 |  | F₃C—φ— | CH₃ | CH₃ | H | OEt | 50 |  |  |
| 58 |  | F₃C—φ— | CH₃ | CH₃ | H | O—CH(CH₃)₂ | 75 |  |  |
| 59 |  | F₃C—φ— | CH₃ | CH₃ | H | O(CH₂)₂N-piperidine HCl | 106 |  |  |

*Obtained from compound No. 8 by a Br → OMe exchange, using sodium methylate.
**Obtained from commercial 3-hydroxyacetophenone.

***Obtained directly from Cl—φ—C(=O)—φ—OH (with OH ortho) (melting point 190° C.), itself obtained by a Friedel-Crafts reaction between Cl—φ—COCl and veratrole.

TABLE III $$R-\underset{\underset{R'''}{|}}{\overset{R}{C}}R-\underset{\underset{2\ 3}{\overset{6\ 5}{\bigcirc}}}{\phantom{C}}\overset{X}{\underset{\underset{R''}{\overset{R'}{|}}}{\phantom{C}}}$$
$$O-\underset{\underset{R''}{|}}{\overset{R'}{C}}-COY$$

| Compound No. | Code No. | R | R' | R" | R''' | X | Y | M.P., °C. | $n_D^{20}$ |
|---|---|---|---|---|---|---|---|---|---|
| 60 | 560 | Cl—φ— | CH₃ | CH₃ | OH | H | OH | 116 | — |
| 61 | 560 A | Cl—φ— | CH₃ | CH₃ | OH | H | OCH₃ | — | 1.553 |
| 62 | 603 | Br—φ— | CH₃ | CH₃ | OH | H | OH | 132 | — |
| 63 | 603 A | Br—φ— | CH₃ | CH₃ | OH | H | O—CH(CH₃)₂ | — | 1.555 |
| 64 | 604 | MeO—φ— | CH₃ | CH₃ | OH | H | OH | 135 | — |
| 65 | 604 A | MeO—φ— | CH₃ | CH₃ | OH | H | OCH(CH₃)₂ | — | 1.542 |
| 66 | 605 | Cl—φ— | CH₃ | CH₃ | —OC(=O)CH₃ | H | OCH(CH₃)₂ | — | 1.5282 |

TABLE III-continued

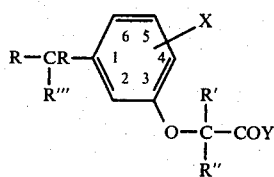

| Compound No. | Code No. | R | R' | R'' | R''' | X | Y | M.P., °C. | $n_D^{20}$ |
|---|---|---|---|---|---|---|---|---|---|
| 67 | 610 | Cl-φ- | CH₃ | CH₃ | OH | H | OCH(CH₃)₂ | — | 1.545 |
| 68 | 620 | Cl-φ- | CH₃ | CH₃ | OCH₃ | H | OH | 119 | — |
| 69 | 657 | Cl-φ- | CH₃ | CH₃ | H | H | OH | 114 | — |
| 70 | 664 | Cl-φ- | CH₃ | CH₃ | H | H | OCH(CH₃)₂ | — | 1.531 |
| 71 | 687 | F-φ- | CH₃ | CH₃ | OH | H | OCH₃ | — | 1.539 |
| 72 | 688 | F-φ- | CH₃ | CH₃ | OH | H | OH | 96 | — |

TABLE IV

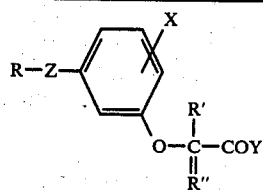

| Product No. | Code No. | R | R' | R'' | X | Z | Y | M.P., °C. | $n_D^{20}$ |
|---|---|---|---|---|---|---|---|---|---|
| 73 | — | F-φ- | CH₃ | CH₃ | H | —C(=CH₂)— | OH | oil | — |
| 74 | — | F-φ- | CH₃ | CH₃ | H | —C(CH₃)OH— | OEt | — | 1,498 |

TABLE V

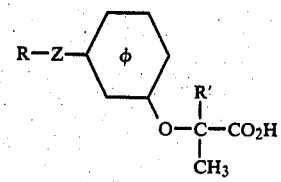

| Product No. | Code No. | R | Z | R' | PERCENTAGE REDUCTION OF TOTAL LIPIDS | PERCENTAGE REDUCTION OF TOTAL CHOLESTEROL |
|---|---|---|---|---|---|---|
| 1 | 451 | Cl-φ- | —CO— | CH₃ | 36.5 | 35 |
| 6 | 539 | Cl-φ- | —CO— | H | 22 | 25 |
| 7 | 561 | Br-φ- | —CO— | CH₃ | 25 | 29 |

TABLE V-continued

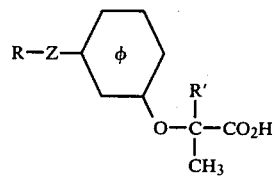

| Product No. | Code No. | R | Z | R' | PERCENTAGE REDUCTION OF TOTAL LIPIDS | PERCENTAGE REDUCTION OF TOTAL CHOLESTEROL |
|---|---|---|---|---|---|---|
| 9 | 576 | 4-Cl-φ | —CO— | CH₃ | 20 | 25 |
| 12 | 599 | φ | —CO— | CH₃ | 17 | 27 |
| 18 | 623 | 4-F-φ | —CO— | CH₃ | 19 | 31.5 |
| 20 | 650 | 3-CF₃-φ | —CO— | CH₃ | 33 | 30 |
| 25 | 686 | 3-CH₃-4-F-φ | —CO— | CH₃ | 49 | 29 |
| 26 | 690 | 2-Cl-φ | —CO— | CH₃ | 20 | 22 |
| 27 | 691 | 4-CF₃-φ | —CO— | CH₃ | 49 | 40 |
| 60 | 560 | 4-Cl-φ | —CHOH— | CH₃ | 35 | 32 |
| 62 | 603 | 4-Br-φ | —CHOH— | CH₃ | 25.5 | 30.5 |
| 69 | 657 | 4-Cl-φ | —CH₂— | CH₃ | 32 | 32 |

I claim:

1. A compound of the formula:

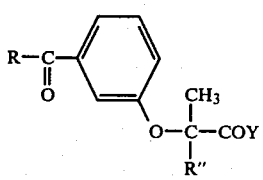

wherein R is a member selected from the group consisting of 4-chlorophenyl, 3-chlorophenyl, 4-bromophenyl, phenyl, 4-methoxyphenyl, 4-fluorophenyl, and 4-trifluoromethylphenyl; R" is a member selected from the group consisting of hydrogen and $C_1$-$C_4$ alkyl; and Y is a member selected from the group consisting of straight and branched $C_1$-$C_{12}$ alkoxy.

2. The compound of claim 1, wherein R" is hydrogen or methyl and Y is methoxy, ethoxy or isopropoxy.

3. The compound of claim 1, wherein R is 4-chlorophenyl, R" is methyl and Y is methoxy, ethoxy or isopropoxy.

4. The compound of claim 1, wherein R is 4-chlorophenyl, R" is hydrogen and Y is isopropoxy.

5. The compound of claim 1, wherein R is 4-bromophenyl, R" is methyl and Y is isopropoxy.

6. The compound of claim 1, wherein R is 3-chlorophenyl, R" is methyl and Y is methoxy.

7. The compound of claim 1, wherein R is phenyl, R" is methyl and Y is isopropoxy.

8. The compound of claim 1, wherein R is 4-methoxyphenyl, R" is methyl and Y is isopropoxy.

9. The compound of claim 1, wherein R is 4-fluorophenyl, R" is methyl and Y is isopropoxy.

10. The compound of claim 1, wherein R is 4-trifluoromethylphenyl, R" is methyl and Y is isopropoxy.

11. A therapeutic composition for the treatment of cardiovascular illness, comprising a therapeutically effective amount of at least one compound according to claim 1, in association with a physiologically acceptable excipient.